US007771632B2

(12) United States Patent
Ghebre-Sellassie et al.

(10) Patent No.: US 7,771,632 B2
(45) Date of Patent: Aug. 10, 2010

(54) CONTINUOUS MELT SPHERONIZATION APPARATUS AND PROCESS FOR THE PRODUCTION OF PHARMACEUTICAL PELLETS

(75) Inventors: Isaac Ghebre-Sellassie, Morris Plains, NJ (US); Charles Martin, High Bridge, NJ (US); Bert Elliot, Highlands, NJ (US)

(73) Assignees: American Leistritz Extruder Corp., Somerville, NJ (US); Pharmaceutical Technology Solutions, LLC, Morris Plains, NJ (US)

( * ) Notice: Subject to any disclaimer, the term of this patent is extended or adjusted under 35 U.S.C. 154(b) by 748 days.

(21) Appl. No.: 11/434,041

(22) Filed: May 15, 2006

(65) Prior Publication Data

US 2007/0264328 A1 Nov. 15, 2007

(51) Int. Cl.
*B28B 1/08* (2006.01)
*A61K 9/14* (2006.01)
(52) U.S. Cl. .................................. 264/69; 424/489
(58) Field of Classification Search ....................... None
See application file for complete search history.

(56) References Cited

U.S. PATENT DOCUMENTS 4,770,625 A * 9/1988 Appelgren et al. .......... 425/331

5,552,159 A 9/1996 Mueller

FOREIGN PATENT DOCUMENTS

| WO | WO 93/07859 | 4/1993 |
| WO | WO 02/35991 A2 | 5/2002 |

OTHER PUBLICATIONS

Nicolas Follonier, et al., Various ways of modulating the release of dilitiazem hydrochloride from hot-melt extruded sustained release pellets prepared using polymeric materials, Journal of Controlled Release, Mar. 1995, 243-250, 36.
Nicolas Follonier, et al., Evaluation of Hot-Melt Extrusion as a New Technique for the Production of Polymer-Based Pellets for Sustained Release Capsules Containing High Loadings of Freely Soluble Drugs, Drug Development and Industrial Pharmacy, 1994, 1323-1339, 20(8).

* cited by examiner

*Primary Examiner*—S. Tran
(74) *Attorney, Agent, or Firm*—Caesar, Rivise, Bernstein, Cohen & Pokotilow, Ltd.

(57) ABSTRACT

Spherically-shaped pharmaceutical pellets are produced using a novel spheronization apparatus in a continuous melt spheronization process in which an active pharmaceutical agent is blended with various excipients, fed to an extruder, cut and subsequently fed to the novel spheronizer for continuously producing uniform, spherically-shaped pellets. The pellets may be further coated so as to provide immediate or various modified release characteristics.

6 Claims, 6 Drawing Sheets

CONTINUOUS MELT SPHERONIZATION APPARATUS AND PROCESS FOR THE PRODUCTION OF PHARMACEUTICAL PELLETS

FIELD OF THE INVENTION

This invention describes the production of pharmaceutical formulations and, in particular, a novel continuous melt spheronization apparatus and process for the production of pharmaceutical pellets.

BACKGROUND OF THE INVENTION

Drug-loaded pellets or beads are specialized drug delivery systems that have been used successfully to develop products that control the release of active ingredients in the gastrointestinal tract at predetermined rates.

A number of pellet or bead manufacturing processes have been developed for the production of pharmaceutical products. The most popular processes utilize organic or aqueous solvents to facilitate pellet production, and can be classified into three categories: solution/suspension layering; powder layering; and wet granulation/extrusion/spheronization. Typically, pellet cores are dried and coated with functional coatings, films or layers to generate controlled release pharmaceutical formulations that are subsequently filled in hard shell gelatin capsules or compressed into tablets.

Solution/suspension layering is generally utilized only when pellets with a low drug loading capability are desired; for high drug loading, the processing times tend to be too long. The layering process is relatively simple and utilizes any conventional coating equipment, although fluid bed machines, due to their high drying efficiency, are the equipment of choice. Powder layering, probably the oldest pharmaceutical pelletization process, utilizes equipment that range from convention coating pans to highly specialized centrifugal fluid bed equipment. In this process, the powder is layered on starter seeds with the simultaneous application of a binder solution.

Extrusion/spheronization is a process where the active ingredient and excipients are sequentially blended, wet-granulated, extruded and spheronized to form pellets. Spheronization is a multi-step process that is employed mainly when pellets with very high drug loading capacities are needed to accommodate high dose products.

Recently, attempts have been made to prepare spherical pellets by melt-spheronization using heat-jacketed spheronizers or marumerizers that are commonly used in wet extrusion/spheronization. For example, published International Patent Application Nos. PCT WO 02/35991 A2 and WO 93/07859 disclose hot-melt extrusion/spheronization processes for manufacturing spherical particles, e.g., active agent-containing pellets or beads. Both applications assert that the processes can be continuous while also eliminating the need for water or organic solvents. However, in both inventions the extrusion and cutting steps are continuous while the spheronization step is in a batch mode. This is made clear in several of the Examples set forth in PCT application WO 02/35991 A2 where it is described that the pellets are cooled to room temperature after being cut in the pelletizer and before being transferred to the spheronizer. Also, it is implicit in WO 93/07859 that the spheronization step is a batch process. This is evident by the use of a Luwa spheronizer which is batch process equipment whose output can only increase by increasing the size of the equipment as opposed to, for example, increasing the processing time as is the case with continuous processors. Thus, unlike the present invention, the processes described in the PCT applications are batch-based and hence prone to the shortcomings associated with typical batch manufacturing processes. Moreover, melt spheronization using conventional marumerization equipment often leads to tacky pellets that tend to agglomerate during manufacturing. This problem could be alleviated by the addition of dusting powder, a procedure that may not necessarily satisfy the requirements of process validation.

The present invention relates to a novel continuous melt spheronization apparatus and process whereby an active ingredient and appropriate excipients are blended and formed into spherically-shaped particles or pellets. The present invention eliminates the need for water or organic solvents and provides particles that fall within a narrow particle size range. As a result, water sensitive drugs and materials can also be employed without running the risk that the drug will be affected by the presence of the solvent. The pellet cores may be further coated with materials such as sugars, polymers, waxes and the like. The coatings of the present invention may also be tailored to the particular need for drug delivery and may be designed to produce immediate, enteric or modified release products.

SUMMARY OF THE INVENTION

The present invention describes a continuous melt spheronization apparatus and process that does not only overcome the deficiencies of the current spheronization equipment and processes identified above, but also will be an integral part of a continuous product manufacturing stream comprising of dispensing, blending, melting, mixing, extruding, cutting, spheronization, cooling, capsule filling and packaging operations, all monitored, tested and controlled in-line.

More specifically, the present invention concerns a novel apparatus and method for producing drug loaded spherically-shaped pellets (e.g., spheroids) by a continuous spheronization process. An active pharmaceutical agent is blended with necessary excipients and is then extruded under appropriate melting temperatures. The extrudate is then cut and cylindrical pellets are spheronized to yield substantially uniform, equal-sized pellets which may have immediate or various modified release properties depending on the active agent, the added excipients and any further coatings which may be applied. No solvents, aqueous or organic, are required during the hot melt extrusion and spheronization. The process is a continuous, as opposed to a batch, operation.

BRIEF DESCRIPTION OF THE SEVERAL VIEWS OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE INVENTION

The novel continuous melt spheronization apparatus and process of the present invention provide numerous advantages over those of the prior art. The process not only obviates the need for the use of hazardous organic solvents but also does away with the use of aqueous media in lieu thereof in the formulation during processing.

Pharmaceuticals that may be pelletized according to the process of the present invention are numerous and varied. Suitable classes of bio-active agents include, but are not limited to, analgesics, anti-inflammatory agents, antibiotics, anti-depressants, anti-epileptics, antihypertensive agents, neutoleptics, corticosteroids, lipid regulating agents, antacids, laxatives, anti-ulcer agents, anti-arrhythmic agents, those known or to be developed in the art, and combinations and/or mixtures thereof.

Figure 1:
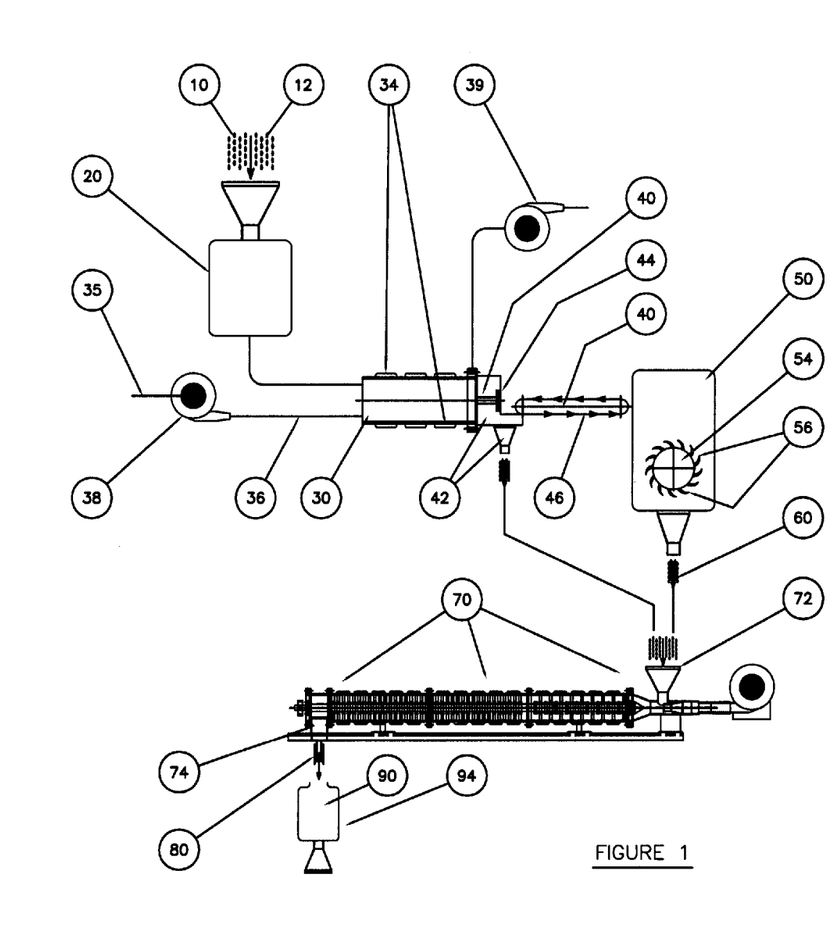
FIG. 1 is a block diagram of a continuous melt spheronization for the production of pharmaceutical pellets in accordance with the present invention.

Referring now to the various drawings wherein like reference characters refer to like parts, FIG. 1 shows a pharmaceutically active ingredient 10 is first blended with appropriate excipients 12 in an appropriate mixer 20 at a suitable speed until a homogeneous blend is obtained. For example, mixers such as planetary and high intensity mixers, V-blenders, cone blenders, etc. are useful in thoroughly mixing the active ingredient 10 and the excipients 12 (formulation components). Suitable excipients include, but are not limited to, all water soluble and insoluble polymers such as cellulose derivatives, starches and their derivatives, polyvinyl pyrrolidine (PVP), acrylic polymers, and waxes as well as inorganic additives such as calcium phosphate, calcium sulfate, talc, aluminum silicate, those known or to be developed in the art, and combinations and/or mixtures thereof. Surfactants, lubricants, binders, pH buffering compounds, plasticizers, other excipients, those known or to be developed in the art, and combinations and/or mixtures thereof may be added to the formulation directly or, if desired, from an aqueous or alcoholic medium.

Formulation components 10 and 12 are charged into the mixer 20 and then fed as a pre-blend at a predetermined rate directly into an extruder 30, having one or more heating zones 34. Alternatively, the formulation components 10 and 12 can also be fed into the extruder 30 simultaneously from separate powder feeders (not shown). Also, if desired, liquid components 35 are fed into the extruder 30 concurrently through one or more ports 36 using one or more pumps 38. The formulation components 10, 12 are mixed with the liquid components 35, when applicable, within the extruder 30. As necessary, trapped air or residual moisture (vapor) in the formulation is removed by a vacuum pump 39.

The extruder 30 is run at temperatures that are of a degree sufficient to melt or soften one or more of the formulation components 10, 12 so as to form a congealed mass of product (extrudate) 40 as the mass 40 exits a die assembly 42 attached to an end of the extruder 30. Thus, the extrudate 40 is extruded at appropriate melting temperatures governed by the type of active ingredient and excipients that make up the pharmaceutical formulation. Those of ordinary skill in the art will appreciate that various different types of extruders 30 and die assemblies 42 can be used within the spirit and scope of the present invention. For example, a Leistritz extruder, American Leistritz Extruder Corporation, Somerville, N.J., and a pelletizing die manufactured by Gala Industries, Eaglerock, Va. can be used as part of the present invention.

The extrudate 40 is extruded axially through the die assembly 42, configured with a desired size of holes or nozzles (not shown). The width of the extrudate 40 is determined by the size of the die holes and the rate at which the extrudate 40 is fed into a cutter or pelletizer 50. The size of the die holes employed should range from about 0.1 mm to about 10 mm, and preferably about 0.6 mm to about 4.0 mm in diameter while the rate at which the extrudate 40 is fed into the pelletizer 50 should range from about 0.05 mm/sec to about 100 mm/sec, and preferably about 0.05 to about 50 mm/sec.

The extrudate 40 is then cut into cylindrical or semi-cylindrical segments or rods 60 either at the die face 44 or by the cutter or pelletizer 50. If the extrudate 40 is cut at the die face 44, then the segments or rods 60 are not fed to the pelletizer 50. If the extrudate 40 is not cut at the die face 44, then the extrudate 40 is fed either directly or via a conveyor belt 46 into the pelletizer 50, such as a Leistritz pelletizer, American Leistritz Extruder Corporation, Somerville, N.J., where the extrudate 40 is cut into the segments or rods 60. The length of the segments or rods 60 depends upon the dimensions of the pelletizer 50 cutting assembly 54 and the blades or knives 56 contained thereon. Generally, the segments or rods 60 range in length from about 0.1 mm to about 10.0 mm, and preferably about 0.5 mm to about 4.0 mm.

After the extrudate 40 is cut into cylindrical or semi-cylindrical segments or rods 60 either at the die face 44 or by the pelletizer 50, the cylindrical or irregular shaped segments 60 are transferred into an inlet port 72 of a spheronizer 70. The segments 60 are fed either directly or via a second conveyor belt (not shown) to the spheronizer 70. The spheronizer 70 forces the segments 60 to rapidly bounce and tumble about the confines of the spheronizer 70 colliding with the internal components of the spheronizer 70 as well as with one another. This motion compacts each segments 60 as well as rounding its ends to a more spherical shape. The spheronizer 70 of the present invention is a specially designed spheronization device which uses particle collisions and, if desired, forced air to create spherically-shaped pellets 80. These spherically-shaped pellets 80 or, as they are sometimes referred to, spheroids are drug delivery particles comprising the pharmaceutically active ingredient 10 and the excipients 12. The spheronizer 70 has an outlet port 74 through which the spherically-shaped pellets 80 exit the spheronizer 70.

After exiting the spheronizer 70, the spherically-shaped pellets 80 are conveyed to a hopper 90 of a capsule-filling machine 94 and subsequently filled into capsules or packaged in-line. Alternatively, the pellets 80 can be collected and stored for future filling operations. The pellets 80 are mono-sized and pack uniformly and consistently, thereby ensuring the production of a high quality product. Appropriate sensors are placed at critical points in the continuous process of the present invention to allow real time monitoring of the process and testing of the pharmaceutical components, mixtures and product.

A number of specially designed spheronizers 70 are envisioned in the present invention. In general, the spheronizer 70 can be described as a device designed to induce particle rolling motion, as well as particle-to-particle, particle-to-wall and particle-to-agitator collisions in order to continuously produce spherically-shaped pellets. The spheronizer 70 of the present invention is temperature controlled and includes a cylindrical tube having a centrally located shaft. Preferably, the spheronizer 70 operates at a wall temperature of about 18° C. to about 150° C. and rotates at about 20 to about 1200 revolutions per minute.

Alternatively, the spheronizer 70 may be a spiral element, much like a condenser, through which the segments 60 are transported and spheronized into spherically-shaped pellets 80. Also, alternatively the spheronizer 70 can be a continuous fluidized bed fitted with the necessary parts to affect spheronization.

If desired or necessary, the formed spherically-shaped pellets 80 are transferred into a cooled chamber (not shown) of the same spheronizer 70 or a second spheronizer (not shown) fitted with a cooling jacket. In the unlikely event that tackiness occurs during processing, anti-adherents could be added to the forming pellets in a controlled manner. Suitable anti-adherents include, but are not limited to, talc, calcium carbonate, magnesium tri-silicate, kaolin, those known or to be developed in the art, and combinations and/or mixtures thereof, and serve to prevent the exudates pieces from sticking together during spheronization. The pellets 80 are generally uniform in size and may vary in diameter from about 0.1 mm to about 10 mm, and preferably about 0.5 mm to about 4.0 mm.

Since the active ingredient 10 is dispersed throughout the matrix, the pellets 80 can be formulated to have immediate or modified release properties depending upon the physicochemical properties of the formulation components. The term "modified release" includes enteric or delayed, extended or sustained, pulsatile and any other release pattern that is not immediate release. The pellets 80 can also be compressed into tablets without significant changes in release profiles.

If desired, the pellets 80 may also be coated with appropriate coating materials to produce immediate, enteric or modified release products. Any coating apparatus, including fluid beds, centrifugal granulators and coating pans, and those to be developed in the art, may be utilized to apply these coatings. For immediate release characteristics, suitable coatings include, but are not limited to, hydroxypropylmethyl cellulose, polyvinyl pyrrolidone (PVP), hydrocypropylcellulose and the like and may be applied in various pellet/coating weight ratios. For enteric release, coatings such as cellulose acetate phthalate (CAP), polyvinyl acetate phthalate (PVAP), methacrylic acid copolymer (MACP), cellulose acetate trimellate, hydroxypropyl methylcellulose phthalate (HP-MCP), those known or to be developed in the art, and mixtures and/or combinations thereof may be used to coat the pellets. Suitable coatings for modified release (stomach/small intestine) include ethyl cellulose methacrylic acid ester copolymers, cellulose acetate and waxes which can also be applied in various ratios.

Figure 2:
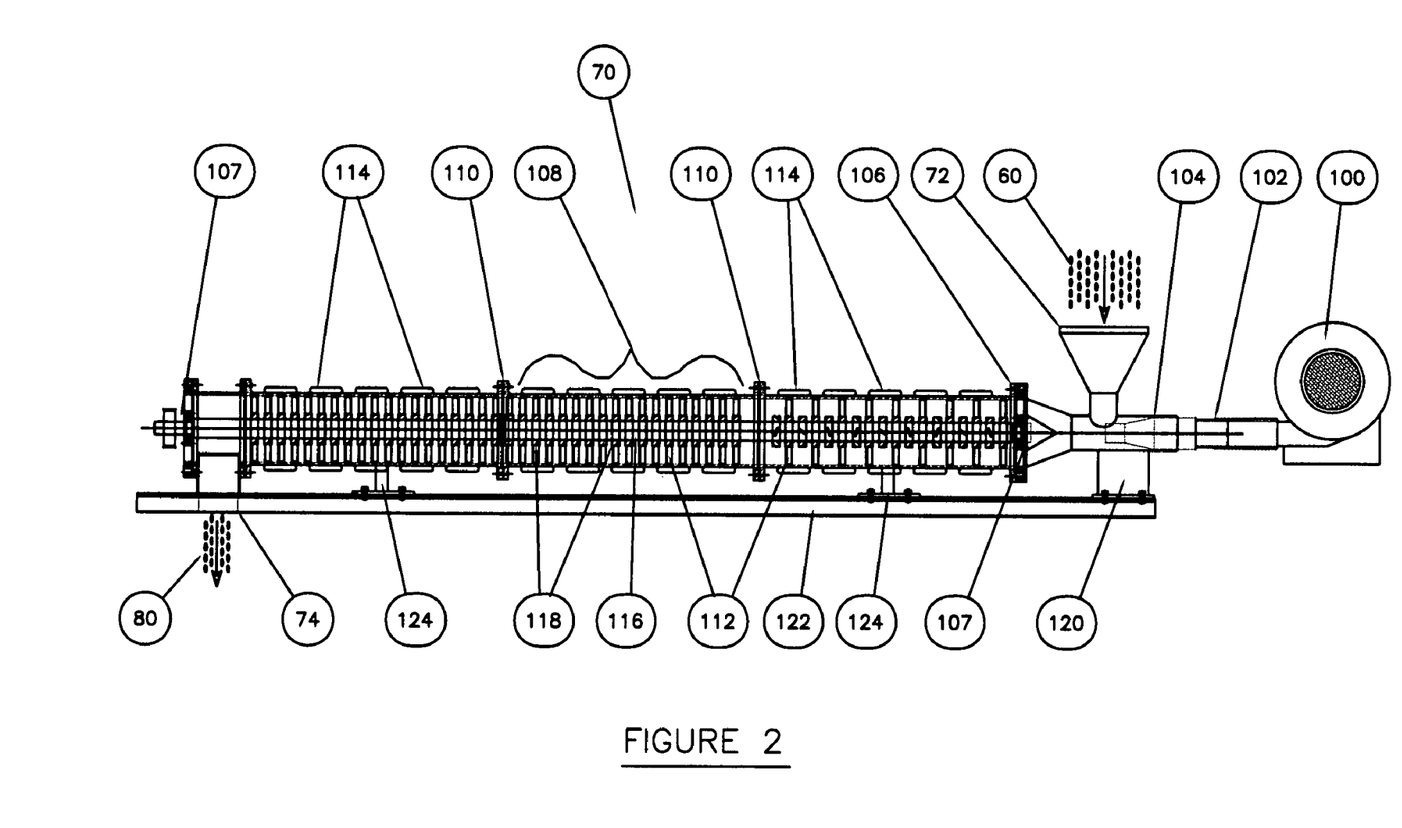
FIG. 2 is a cross-sectional, perspective view of a first embodiment of a cylindrical continuous spheronizer of the present invention.

FIG. 2 shows one embodiment of the spheronizer 70 of the present invention having the inlet port 72 for receiving the cylindrical or semicylindrical shaped segments or rods 60 and the outlet port 74 through which the pellets 80 exit the spheronizer 70. An optional blower 100 provides air to the spheronizer 70 forcing the pellets 60 from the inlet port 72 to the outlet port 74 while also providing heated air to promote spheronization. Preferably, air enters through the blower 100 at a temperature of about 18° C. to about 150° C. It is also preferred that the blower 100 include a variable speed motor controller (not shown) so that the rate at which the segments 60 transit through the spheronizer 70 can be controlled by controlling the speed of the blower 100 such that there is a steady continuous flow of segments 60 from the inlet port 72 to the outlet port 74. It is further preferred that the blower 100 operate at a power output of about 0.5 kW to about 10 kW and provide about 15 to about 1500 cubic feet of air per minute at a velocity of about 1.5 to about 100 meters per second.

The blower 100 is in contact with a hose 102 which acts as a conduit for supplying the air from the blower 100 to a venturi 104. Preferably, the hose 102 is flexible and the venturi 104 is adjustable such that the air velocity can also be controlled by adjusting the venturi 104. If the use of the blower 100 and venturi 104 is not desired or necessary, the spheronizer 70 can be designed such that the inlet port 72 is located further along the length (downstream) of the spheronizer 70 such that the segments 60 do not transit the entire length of the spheronizer 70.

Still referring to FIG. 2, the air exiting the venturi 104 contacts the pellets 60 and forces them past a drive and bearing assembly 106, including a bearing plate 107. The spheronizer 70 includes one or more cylindrical tube sections 108 joined together by at least one clamp 110 to form a cylinder. Preferably, the tube sections 108 are 6 inch schedule 40 steel pipe and about 24 inches in length while the clamps 110 are about 6 inches in length. It is also preferred that the tube sections 108 have an inside diameter of about 2 inches to about 30 inches and have a length to diameter (L/D) ratio of about 4:1 to about 60:1. The tube sections 108 may have a plain smooth interior or may contain blades 112 which are configured and pitched to maximize particle to wall contact and a steady continuous flow of the pellets 60 from the inlet port 72 to the outlet port 74.

It is further preferred that the spheronizer 70 contain at least one heater 114. As shown in FIG. 2, more than one heater 114 can be positioned along the length of the tube sections 108 of the spheronizer 70. Where the tube sections 108 of the spheronizer 70 are not stationary, but instead rotate, the heaters 114 are preferably in the form of radiant heaters and, if desired, separated from each other and separately controlled into heating zones along the length of the spheronizer 70.

A fixed central shaft 116 is also an integral component of the embodiment of the spheronizer 70 shown in FIG. 2. The shaft 116 is supported at both ends by bearing plates 107. The shaft 116 contains numerous stationary blades 118 along its length which are positioned so as to not contact the blades 112 located along the length of the tube sections 108. The shaft 116 functions to increase the number of particle collisions in order to more efficiently produce spherically-shaped pellets.

The embodiment shown in FIG. 2 is further controlled by an optional adjuster 120. The adjuster 120 enables the inlet end of the spheronizer 70 to be elevated higher than the outlet end of spheronizer 70. The rate at which the segments 60 flow through the spheronizer 70 can be adjusted and controlled, in part, by using the adjuster 120 to establish an angle of inclination along the length of the spheronizer 70. Thus, if desired, in addition to the force provided by the air of the blower 100, the adjuster 120 can be used so that the segments 60 are also subjected to a gravitational force established by the angle of inclination between the inlet 72 and outlet 74 of the spheronizer 70. Preferably, the angle of inclination is about 0 degrees to about 30 degrees from a horizontal plane. Alternatively, the spheronizer 70 can be permanently mounted to a solid surface 122 by at least two brackets 124. Preferably, the brackets 124 are adjustable so that they can continue to support the spheronizer 70 when the adjuster 120 is used to establish the angle of inclination.

Figure 3:
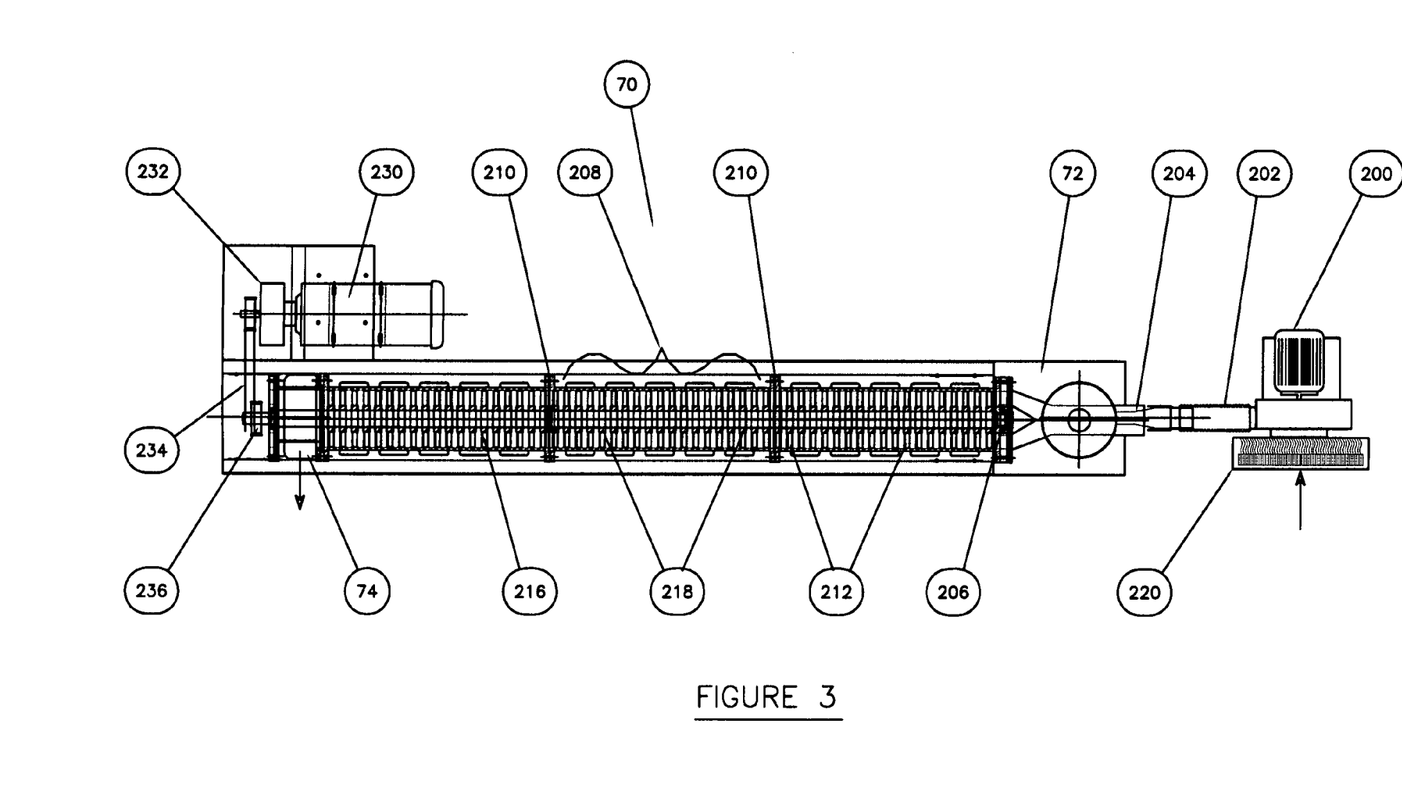
FIG. 3 is a cross-sectional, perspective view of an alternative embodiment of the cylindrical continuous spheronizer of the present invention shown in FIG. 2.

FIG. 3 shows a cross-sectional view of one alternative embodiment of the spheronizer 70 shown in FIG. 2. The embodiment of FIG. 3 is similar to the embodiment of FIG. 2 having many like parts. For example, like FIG. 2, the embodiment of FIG. 3 also includes a blower 200, a hose 202, a venturi 204, a bearing plate 206, tube sections 208, clamps 210, a central shaft 216, and blades 212, 218. The embodiment of FIG. 3 does not, however, have an adjuster for establishing an angle of inclination between the inlet and outlet of the spheronizer 70. It also does not have a plurality of band heaters but instead is capable of pre-heating air entering into the spheronzier 70 by placing a heater 220 in the vicinity of the blower 200. The heater 220 is shown in FIG. 3 as being located at the inlet side of the blower 200; however, it will be appreciated by those of ordinary skill in the art that the heater 220, or multiple heaters, could alternatively be located on the outlet side of the blower 200 and still function within the spirit and scope of the present invention.

Still referring to FIG. 3, a motor 230 is connected to a portion of the spheronizer 70 providing another means by which a portion of the spheronizer 70 and, in particular, the tube sections 208, rotate during operation of the spheronizer 70. Preferably, the motor 230 has a variable speed controller (not shown) capable of operating at a power of about 0.5 kW to about 10 kW so that the rate at which the tube sections 208 rotate can be controlled such that there is a steady, continuous flow of segments 60 from the inlet port 72 to the outlet port 74. The motor 230 can be either an alternating or direct current (AC or DC) motor and be either hydraulic or pneumatic. Preferably, the motor 230 has a cylindrical drive having variable speeds (0 to 100%) and is connected to a reduction gear 232 having a ratio of about 1:1 to about 100:1 which converts the high speed of the motor to a lower speed for rotating the spheronizer 70. A timing belt 234 connects the reduction gear to a clamping flange 236 located toward the outlet end of the spheronizer 70. Preferably, the tube sections 108 of the spheronizer 70 rotate at about 20 rpm to about 1200 rpm.

Figure 4:
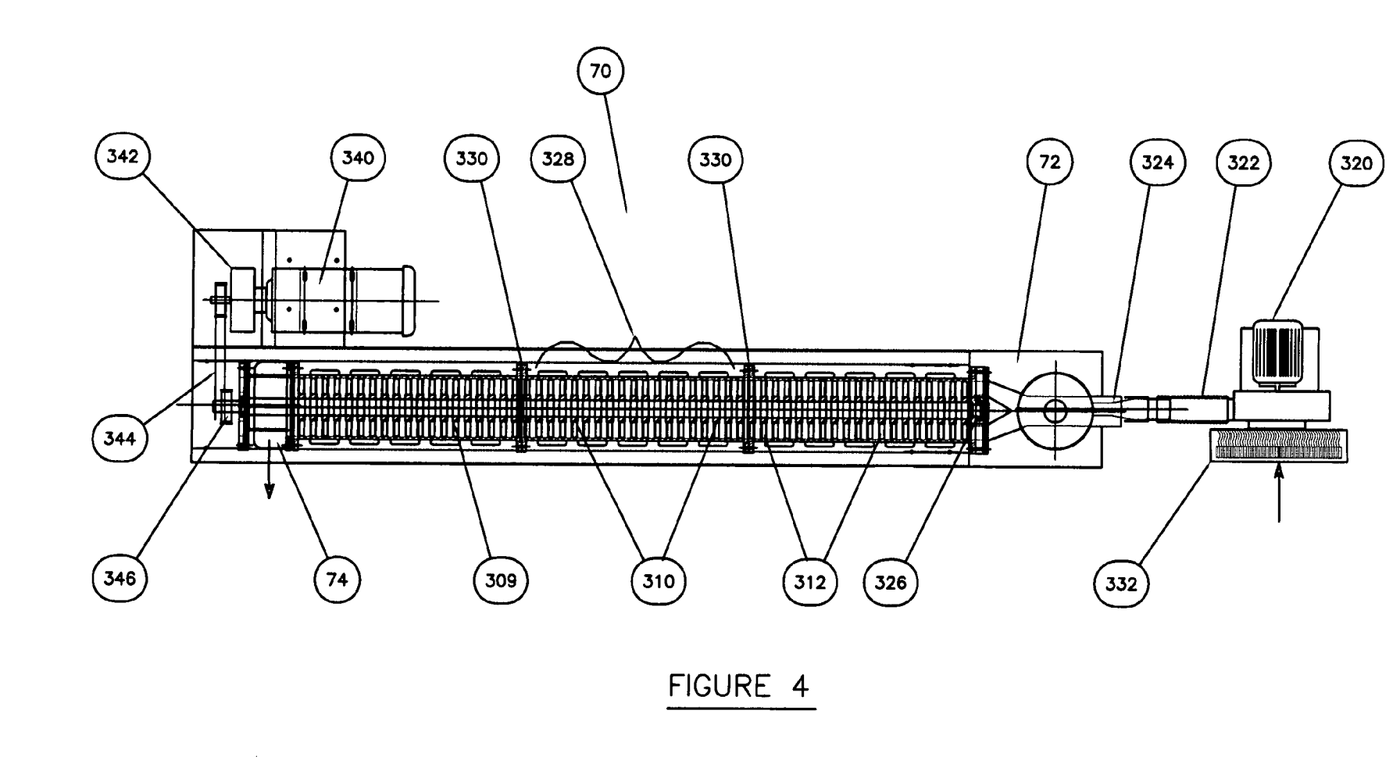
FIG. 4 is a cross-sectional, perspective view of another alternative embodiment of a cylindrical continuous spheronizer of the present invention.

Referring now to FIG. 4, another embodiment of the present invention is shown wherein cylindrical tube sections 328 are stationary and a central shaft 309, having blades 310, rotate within the joined tube sections 328 of the spheronizer 70. The embodiment of FIG. 4 is similar to the embodiments of FIGS. 2 and 3 having many like parts. For example, like the embodiments in FIGS. 2 and 3, the embodiment in FIG. 4 also includes blades 310, 312, blower 320, a hose 322, a venturi 324, a bearing plate 326, tube sections 328, clamps 330, and a heater 332.

As in FIG. 3, a motor 340 is connected to a portion of the spheronizer 70 in the embodiment of FIG. 4. However, instead of enabling the tube sections 328 to rotate during operation of the spheronizer 70, the motor 340 in the embodiment shown in FIG. 4 rotates the central shaft 309. As in the embodiment shown in FIG. 3, preferably, the motor 340 has a variable speed controller (not shown) capable of operating at a power of about 0.5 kW to about 10 kW so that the rate at which the central shaft 309 rotates can be controlled such that there is a steady, continuous flow of segments 60 from the inlet port 72 to the outlet port 74. The motor 340 can be either an alternating or direct current (AC or DC) motor and be either hydraulic or pneumatic. Preferably, the motor 340 has a cylindrical drive having variable speeds (0 to 100%) and is connected to a reduction gear 342 having a ratio of about 1:1 to about 100:1 which converts the high speed of the motor to a lower speed for rotating the spheronizer 70. A timing belt 344 connects the reduction gear 342 to a clamping flange 346 located toward the outlet end of the spheronizer 70. Preferably, the central shaft 309 rotates at about 20 rpm to about 1200 rpm.

It will be appreciated by those of ordinary skill in the art that various combinations of the embodiments shown in FIGS. 2-4 can be used within the spirit and scope of the present invention. For example, the embodiment shown in FIG. 2 can further comprise the motor 230, reduction gear 232 and timing belt 234 shown in FIGS. 3 and 4, while the embodiments of FIGS. 3 and 4 can further comprise the adjuster 116 shown in FIG. 2.

Figure 5:
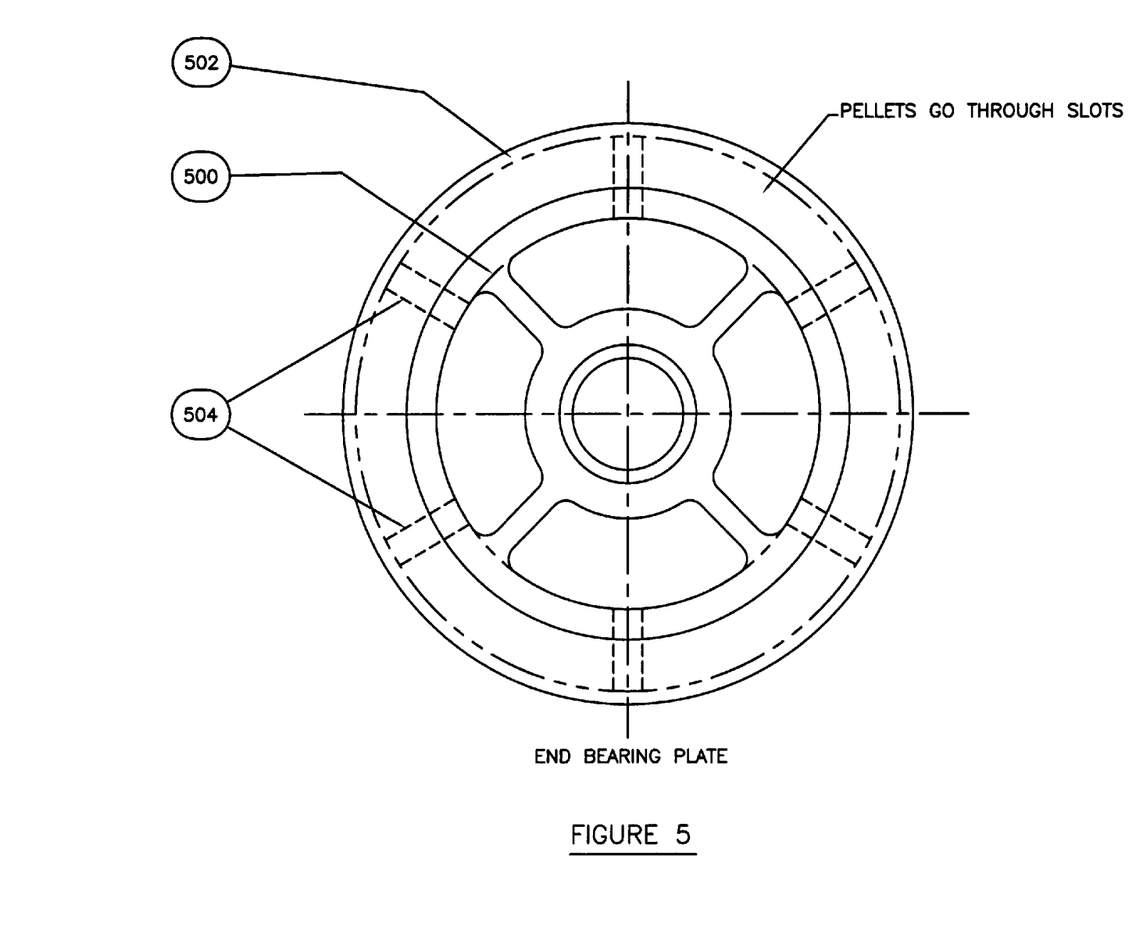
FIG. 5 is an enlarged view of a bearing plate of the cylindrical continuous spheronizer of the present invention.

Referring now to FIG. 5, a cross-sectional view of the bearing plates 106, 206, 326 shown in FIGS. 2-4 is enlarged and depicted in greater detail. Preferably, the bearing plate 106, 206, 326 is cylindrical and fits within the cylindrical tube sections 108, 208, 328 of the spheronizer 70. It is also preferred that the bearing plate include a plurality of openings or slots having an inner wall 500, an outer wall 502 and at least two side walls 504. When the spheronizer 70 is in operation, the bearing plate 106, 206, 326 is held in place by contact of the inner wall 500 and outer wall 502 with the central shaft 116, 216, 309 and the tube sections 108, 208, 329, respectively of the spheronizer 70. If desired, the bearing plate 107, 206, 326 can be removed from the spheronizer 70 to, for example, clean or replace it. The segments 60 pass through the slots of the bearing plate 107, 206, 326 and proceed along the long axis of the spheronizer 70 where they collide with each other as well as with the internal components of the spheronizer 70. It will be appreciated by one of ordinary skill in the art that the bearing plate 107, 206, 326 can have a plurality of side walls 504 such that there are a plurality of openings or slots for segments 60 to pass through the bearing plate 107, 206, 326.

Figure 6A:
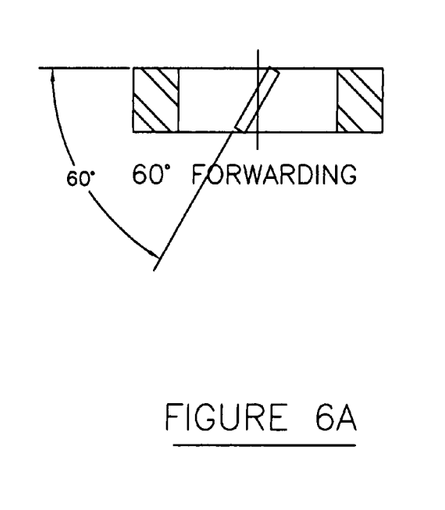
FIG. 6 is an enlarged view of three alternative blade positions of the cylindrical continuous spheronizer of the present invention.
Figure 6B:
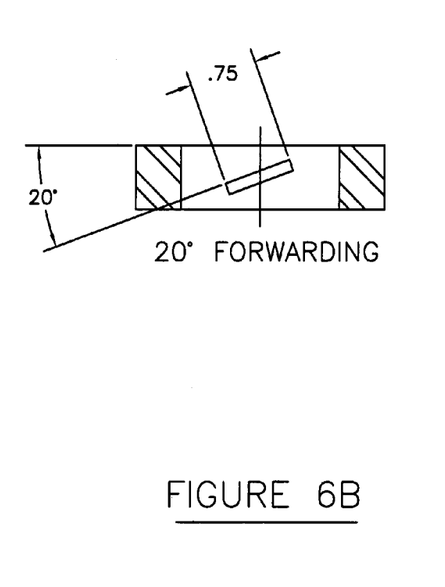
Figure 6C:
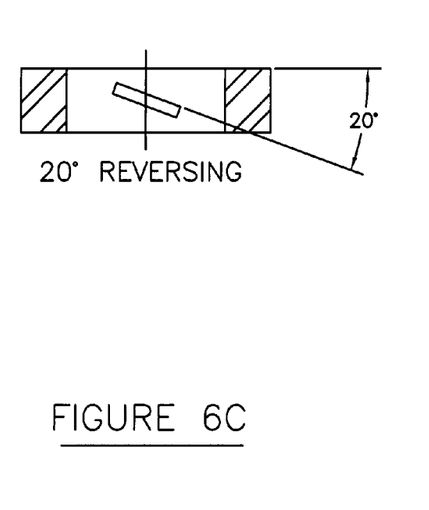

FIGS. 6A-6C shows an enlarged view of the blades 112, 118, 212, 218, 310, 312 shown in FIGS. 2-4. FIG. 6A-6C shows three alternatives for placing the blades along either the tube sections 108, 208, 328 or the shaft 116, 216, 309. It is shown that, preferably, the blades are placed at either a 20 degree or 60 degree forward angle, and a 20 degree reverse angle. A forward degree angle will cause the segments 60 to transit along the length of the spheronizer 70 from its inlet to its outlet, while the reverse angle blade will tend to temporarily hold or delay the segments 60, thereby increasing the residence time of the segments 60. Of course, combinations of the three alternative blade configurations can be used in each of the embodiments of the spheronizer 70 of the present invention. Also, a person of ordinary skill in the art will appreciate that various blade sizes can be used and that other blade angles can be used within the spirit and scope of the present invention.

Success of the spheronizer 70 and the manufacturing process described in this invention are contingent upon the properties of the selected formulation components, which are required to possess, in addition to the commonly known pharmaceutical properties, functionalities that are unique to this particular process. In particular, the formulation should include melt spheronization agents that lower the glass transition temperatures of the components and/or soften or melt themselves to induce deformation to the matrices. These agents include waxes, lipids, fatty acids, high boiling liquids or plasticizers, surfactants and low molecular weight polymers.

EXAMPLES

The following examples are provided as further teachings of the present invention so as to better enable one skilled in the art to practice the claimed invention herein. They are for illustrative purposes only, and should not be seen as limiting the spirit and scope of the claims that follow.

Example 1

Ethylcellulose (350 grams), stearic acid (600 grams) and propranol hydrochloric acid (200 grams) are granulated in fluid bed equipment using a solution of hydroxypropyl cellulose (50 grams) in water. The granulation is then fed into a Leistritz twin screw extruder and extruded through a die at extruder barrel temperatures of 30° C. to 95° C. to generate cylindrical strands which are subsequently cut onto into small segments and spheronized in the continuous spheronizer under the following conditions: 60° C.; 200 rpm agitator speed; 50 cfm air volume; 20 meters/second air velocity and 50° C. inlet air temperature. The continuously produced spheroids are collected in a bin for further processing.

Example 2

Polyvinylpyrrolidone (350 grams), genfibrozil (350 grams), polyethylene glycol 6000 (100 grams) and silicon dioxide (20 grams) are blended in a planetary mixer and fed into an Leistritz twin screw extruder and processed as in Example 1. The spheronizer processing conditions are: 40° C. tube wall temperature; 150 rpm agitator speed; 25 cfm air volume; 20 meters/second air velocity; and 40° C. inlet air temperature. The continually produced spheroids are transported online to a hopper of a capsule filling machine to be filled into capsules.

Although illustrated and described herein with reference to certain specific embodiments and examples, the present invention is nevertheless not intended to be limited to the details shown. Rather, various modifications may be made in the details within the scope and range of equivalents of the claims and without departing from the spirit or scope of the invention.

We claim:

1. A continuous-type spheronizer for use in a continuous melt-spheronization pharmaceutical process comprising:
    a) an inlet port for receiving non-spherically shaped pharmaceutical segments;
    b) at least one cylindrical tube section;
    c) a fixed shaft centrally located along said at least one cylindrical tube section;
    d) an outlet port for delivering substantially uniform, about equal-sized, spherically-shaped pellets; and
    e) a motor connected to a portion of the spheronizer to operate the spheronizer, wherein said cylindrical tube section and said shaft comprise blades, at least some of which are angled that continuously mix and direct said segments along said at least one tube section toward said outlet.

2. The spheronizer of claim 1, further comprising a blower for delivering forced air to said at least one tube section.

3. The spheronizer of claim 1, further comprising at least one heater.

4. The spheronizer of claim 1, further comprising an adjuster for setting an angle of inclination from said inlet to said outlet.

5. The spheronizer of claim 1, further comprising a motor assembly for rotating at least one of said shaft and said tube section.

6. The spheronizer of claim 1, further comprising at least one clamp for joining two or more rube sections.

* * * * *